United States Patent [19]

Chappell et al.

[11] 4,447,373

[45] May 8, 1984

[54] PROCESS FOR MAKING FILLED ARTICLES FROM POLYMERIC MATERIAL

[75] Inventors: Charles W. Chappell, West Chester; Eldon G. Spletzer, Cincinnati, both of Ohio

[73] Assignee: The Procter & Gamble Company, Cincinnati, Ohio

[21] Appl. No.: 348,852

[22] Filed: Feb. 16, 1982

[51] Int. Cl.$^3$ .............................................. B29C 6/00
[52] U.S. Cl. .......................................... 264/4; 53/408; 53/433; 156/146; 264/39; 264/85; 264/510; 264/511; 264/512; 264/545; 264/102; 264/248
[58] Field of Search ...................... 264/4, 39, 85, 102, 264/510–512, 545, 248; 156/146; 53/408, 433

[56] References Cited

U.S. PATENT DOCUMENTS

| | | | |
|---|---|---|---|
| 1,146,523 | 7/1915 | Roberts | 156/245 |
| 1,163,987 | 12/1915 | Eggers | 156/120 |
| 1,263,141 | 4/1918 | Strauss | 156/148 |
| 1,365,462 | 1/1921 | Crawford | 264/545 |
| 1,575,388 | 3/1926 | Roberts | 156/81 |
| 2,223,019 | 11/1940 | Gammeter | 18/35 |
| 2,249,612 | 7/1941 | Kalowski | 154/18 |
| 2,323,582 | 7/1943 | Weckesser | 18/21 |
| 2,329,839 | 9/1943 | Kalowski | 18/5 |
| 2,513,852 | 7/1950 | Donofrio | 18/56 |
| 3,269,088 | 8/1966 | Kath | 53/184 |
| 3,773,871 | 11/1973 | Merrill | 264/22 |
| 4,111,201 | 9/1978 | Theeuwes | 128/260 |
| 4,111,202 | 9/1978 | Theeuwes | 128/260 |
| 4,111,203 | 9/1978 | Theeuwes | 128/260 |
| 4,198,976 | 4/1980 | Drobish et al. | 128/260 |
| 4,200,090 | 4/1980 | Drobish | 128/127 |
| 4,248,275 | 2/1981 | Reed | 264/545 X |
| 4,294,859 | 10/1981 | Lundquist et al. | 53/408 X |

FOREIGN PATENT DOCUMENTS 2935603  3/1981  Fed. Rep. of Germany.

Primary Examiner—Jan H. Silbaugh
Attorney, Agent, or Firm—Frost & Jacobs

[57] ABSTRACT

A process of making a hollow article from polymeric material is taught. The article is molded in two parts. The two parts are caused to remain in their respective exterior molds. If the hollow article is to be filled with a desired material, a measured amount of filler material is added to one of the formed parts. The exterior molds are brought into opposed position and sealing relationship. The space between the exterior molds is purged with a purging gas and subjected to a partial vacuum. The exterior molds are then closed and subjected to a clamping pressure to join the part halves together and remove flash from the joint. Portions at least of the exterior molds are heated and then cooled. The exterior molds are then opened, and the finished filled article is removed therefrom.

17 Claims, 19 Drawing Figures

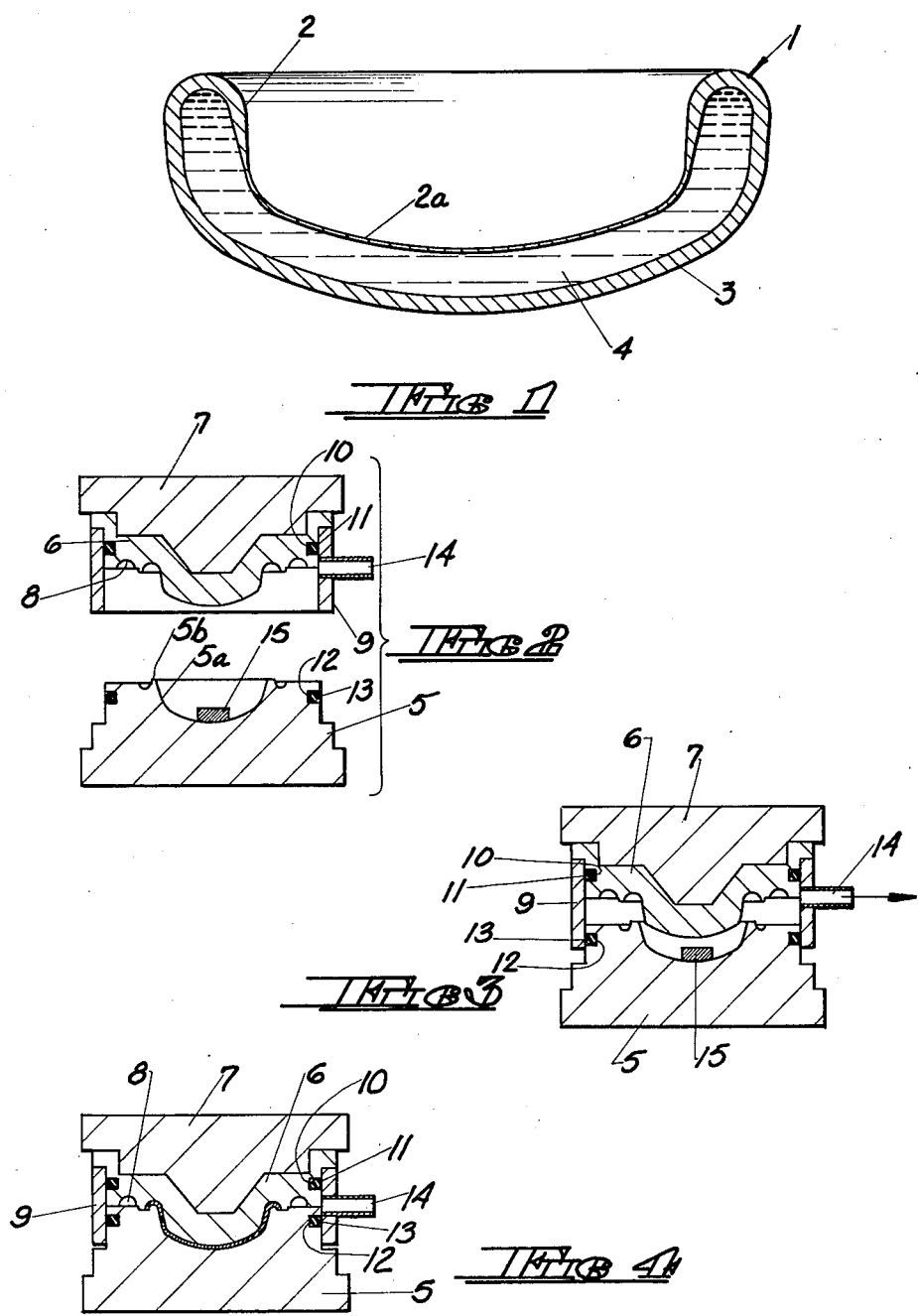

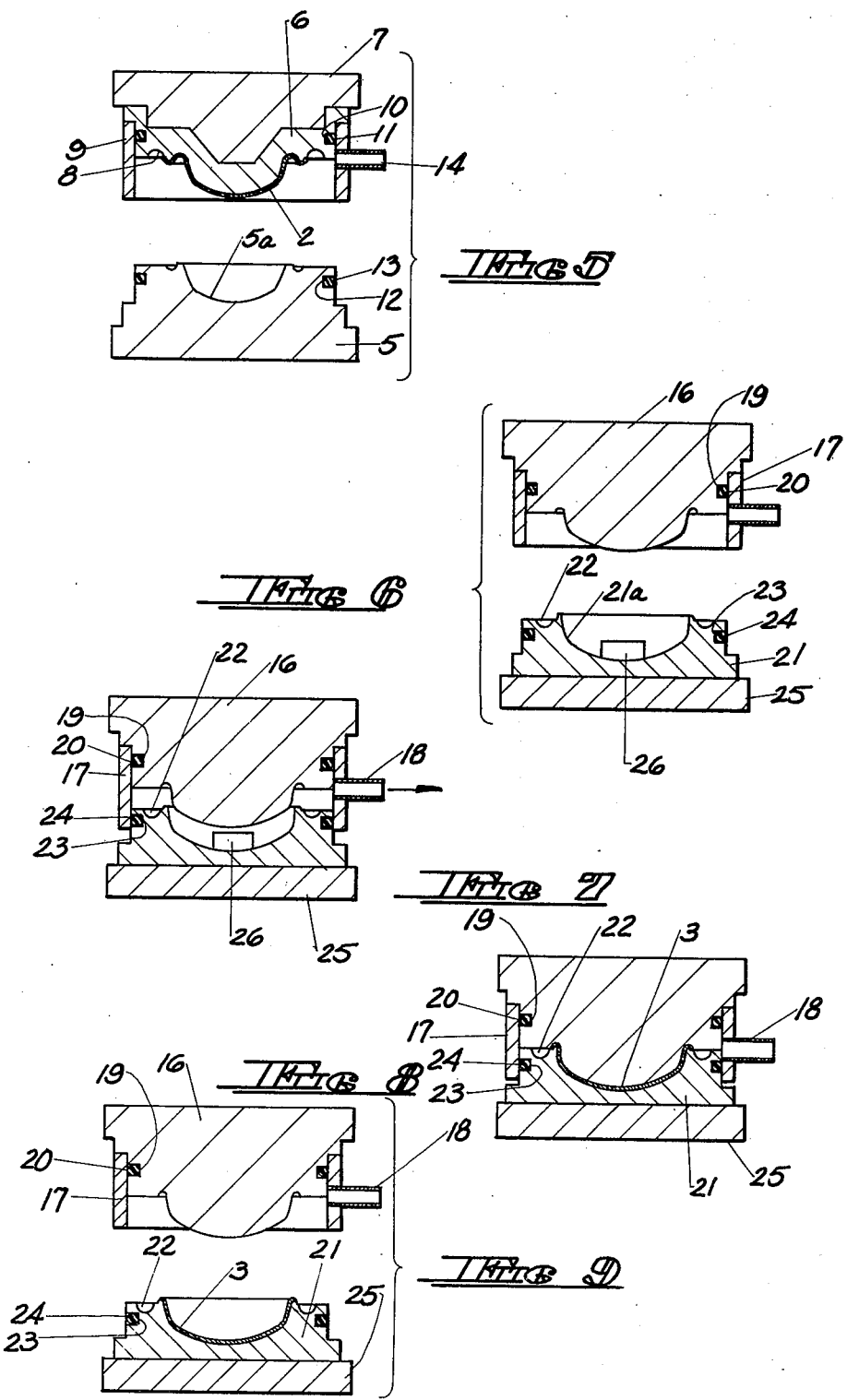

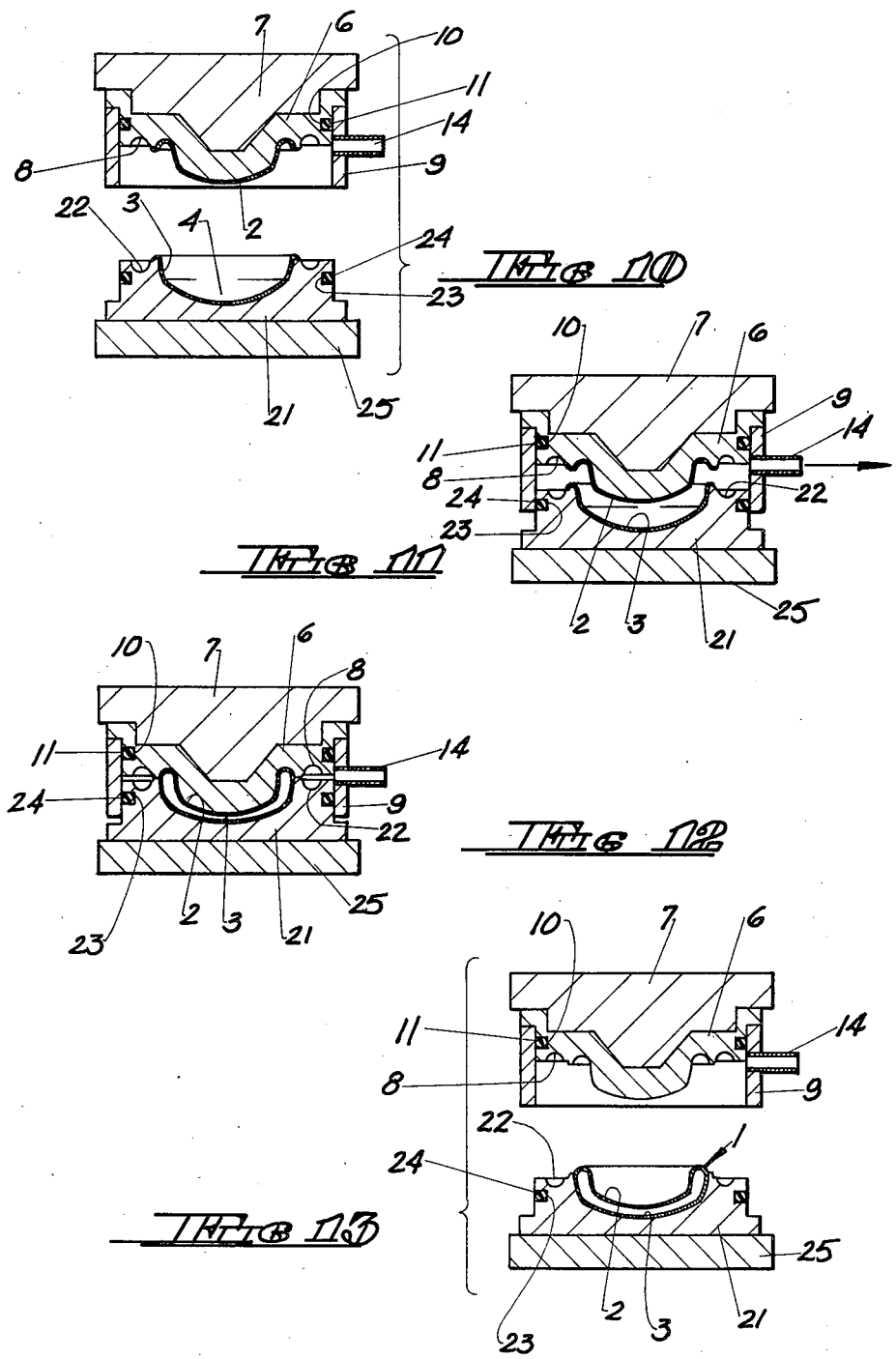

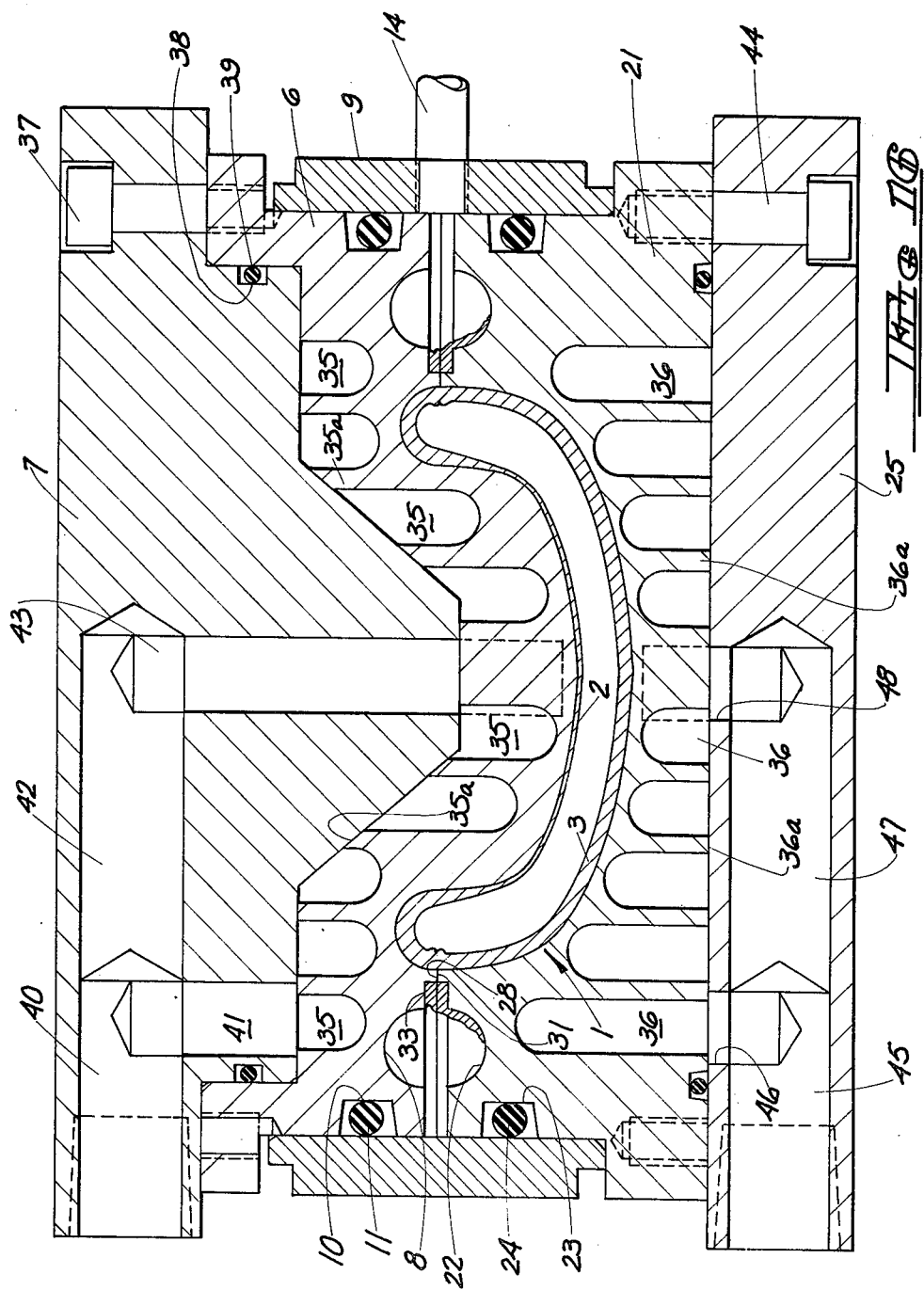

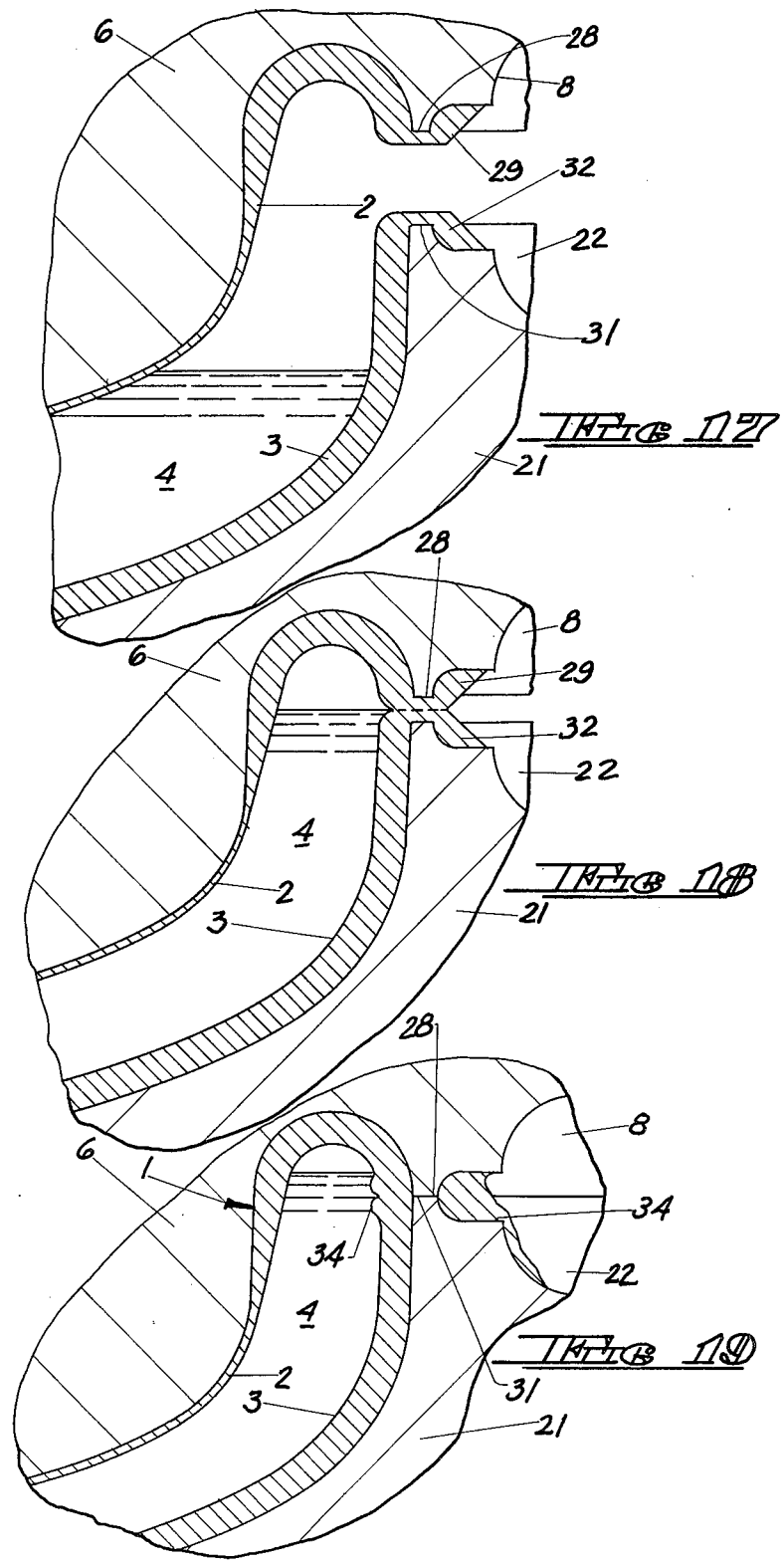

PROCESS FOR MAKING FILLED ARTICLES FROM POLYMERIC MATERIAL

TECHNICAL FIELD

The invention relates to a process for making filled articles from curable polymeric material, and in a particularly preferred embodiment to a form, fill, seal and cure process accomplished in one rapid sequence without removing the article from its forming molds.

BACKGROUND ART

Prior art workers have devised numerous methods for making filled articles from curable, moldable material. The filled articles, themselves, range from golf ball centers and tennis balls, on the one hand, to encapsulated medicaments and contraceptive devices on the other.

One approach to the forming of filled articles is exemplified by U.S. Pat. No. 1,146,523 in the name of F. T. Roberts, issued July 13, 1915, and U.S. Pat. No. 2,223,019 in the name of J. R. Gammeter, issued Nov. 26, 1940 and U.S. Pat. No. 2,329,839 in the name of P. Kalowski, issued Sept. 21, 1943. The latter two patents teach the making of golf ball centers. Both patents involve the forming of hollow rubber balls in two halves, and joining the halves together while immersed in a liquid filling material. U.S. Pat. No. 1,146,523 teaches a method for making inflated rubber articles wherein the hollow rubber article is made in two parts which are joined together while located within a chamber filled with compressed air, the balls being thereafter cured and trimmed of flash.

Yet another approach is taught in U.S. Pat. No. 2,249,612 in the name of P. Kalowski, issued July 15, 1941. In accordance with this reference, a golf ball center is manufactured by drawing a raw rubber sheet into a cup-shaped member. The cup-shaped member is filled with a liquid filling material. The filled cup-shaped member is then capped by a further sheet of raw rubber. This structure is thereafter placed in a perfectly spherical mold and is vulcanized and cured to form the golf ball center.

U.S. Pat. No. 1,163,987 in the name of W. J. Eggers, issued Dec. 14, 1915 and U.S. Pat. No. 1,263,141 in the name of H. R. Strauss, issued Apr. 16, 1918 both teach methods wherein spherical rubber balls are made in two halves. The halves are joined together and the resulting balls are filled with fluid by means of a needle or the like, prior to or during a vulcanizing step.

U.S. Pat. No. 3,773,871 in the name of E. W. Merril, issued Nov. 20, 1973, teaches a process for encapsulating drugs and other therapeutic reagents which can be effused through the encapsulating material. According to this reference two blanks of circular disk-like configuration are formed from uniformly thick sheeted silicone gum stock. These disks are each placed in a shaped mold so as to form a depression in its center portion. This center portion is then subjected to direct ionizing radiation to cross link the polymer. The central depressed portion of each blank is thereafter filled with medicament and the blanks are assembled face to face with the medicament encapsulated therebetween. Gentle pressure is applied to the flange portion of the structure to cause coalescence between the silicone in the flanges. Thereafter, the flange portion of the device is subjected to ionizing radiation so that the flange portion becomes uniformly cross linked.

The method of the present invention for making filled articles from curable polymeric material has many and varied applications. For purposes of an exemplary showing, the process will be described in its application to the manufacture of vaginal contraceptives of the general type taught in U.S. Pat. No. 4,198,976 in the names of J. L. Drobish and T. W. Gougeon, issued Apr. 22, 1980 and U.S. Pat. No. 4,200,090 in the name of J. L. Drobish, issued Apr. 29, 1980.

The teachings of the two last mentioned patents are incorporated herein by reference. Briefly, these references teach devices used in the vagina to deliver spermicidal surfactant. The contraceptive of each of these references is foldable for easy insertion and, once in position at the cervical os, it opens to "cap" the os and remain in position, even during intercourse, so that access of the spermicidal surfactant source to the cervical os is not interrupted. The contraceptive is designed to remain comfortably in the vagina during the time between menstrual periods to provide desirable, prolonged release of a spermicidal surfactant.

In general, the contraceptive of each of these references comprises two dome-shaped or dish-shaped disks which are assembled into an externally rimless structure constituting a container for the spermicidal ingredient. The front or inner face of the device (that surface facing the os) constitutes a membrane permeable by surfactant monomers but not permeable to the passage of surfactant micelles. The outer or rearward portion of the device is less permeable (or impermeable) to surfactant monomers by virtue of being made of a different material, or by being made of the same material and of greater thickness than the front or inner face. The two parts of the device are assembled with their edges sealed together in any suitable fashion such as polymer welding, adhesive sealing, or the like. The completed unit is filled through a thick section using a hypodermic syringe. As a part of this step, air trapped in the unit during sealing has to be bled back into the syringe.

An important feature of the contraceptive devices of these references lies in the fact that each provides a reservoir from which spermicide is released in a controlled manner through the semi-permeable membrane which comprises at least a portion of the inner or front face of the device. The material from which the device is made is such that surfactant micelles cannot diffuse through the semi-permeable membrane. Rather, they must first disassociate to form surfactant monomer molecules which then dissolve in the membrane material and diffuse therethrough to its outer surface. Once so diffused, the surfactant monomers are free to dissolve in the surrounding vaginal fluid to provide their contraceptive effect. The predominant driving force for this diffusion is the concentration difference between unassociated (i.e., substantially monomeric) surfactant molecules in the solution inside and outside the contraceptive device. As a result, the rate of transport through the membrane will slow drastically when the exterior surfactant monomer concentration approaches that on the interior of the device, resulting in the desired controlled release of the surfactant through the membrane. The bulk of the surfactant remains in micellar form, where it resides in reserve within the device to provide a source of monomers over a long period of time, thereby delivering continuous contraceptive protection to the user for a time period of from about 20 to about 30 days.

The method of manufacture taught in the above noted references, comprising the steps of molding an inner or front part and an outer or rear part; gluing the parts together with an appropriate adhesive; filling the completed unit with a hypodermic syringe, and bleeding trapped air back into the syringe, was a slow process which did not lend itself well to commercialization. The present invention is based upon the discovery of a form-fill-seal and cure (where thermosetting materials are employed) process which can be performed in one rapid sequence without removing the unit from its original forming molds. This process is very much faster, dramatically reducing processing time. A more consistent and higher quality product is obtained. Typically less scrap is produced and the process enables more design latitude, since the entire process is carried out without removing the unit from its original forming molds prior to completion.

The process of the present invention enables the forming of uncured parts by compression or injection molding and the joining and curing of these parts to form a hollow filled or unfilled article. The joining step incorporates pinch-off of excess material forming a strong, reinforced, leak-free line seal which is smooth and flash-free at the exterior of the product. While it is generally preferred to maintain the seal area free of extraneous materials, this seal can in some instances be accomplished even when surfactant solutions and mold release agents are present in the seal area as the molds are closing. When the device is to be filled with a liquid, or the like, a novel purge and partial vacuum procedure is provided to minimize the volume of gas in the final cavity and the presence of gas bubbles in the walls of the unit, to eliminate frothing of the active filler material, and to provide a proper balance of liquid and gas within the unit to serve as a strong, resilient, compression molding core.

DISCLOSURE OF THE INVENTION

According to the invention there is provided a process of making a hollow filled or unfilled article from a polymeric material. The article is made in at least two parts by vacuum, compression or injection molding. When compression molding is used, a mold and forming die set is provided for each part. The mold and forming die of each set are brought into sealing relationship with a measured amount of polymeric material therebetween. Preferably the forming die is coated with a release agent. A vacuum is pulled in each set to minimize bubbles and flaws in the part and the part is formed in each set by compression molding. The forming dies of each set are removed with the formed parts remaining in their respective molds.

A measured amount of material to be encapsulated is added to one of the formed parts. The molds are thereafter brought into opposed position and sealing relationship with the molded part halves not yet in sealing relationship. The space between the molds (and thus the space between the part halves) is evacuated of air, purged with a purging gas, and then subjected to a partial vacuum in a vacuum and purge procedure to be described hereinafter. The molds are then fully closed and subjected to clamping pressure to join the part halves together in a strong, leak-free reinforced line seal, the exterior surface of the line seal being rim-free with flash removed by pinch-off. Normally, a small amount of purge gas remains within the article which, together with the incompressible liquid, forms a strong, resilient, compression molding core.

The closed and clamped molds are then heated by appropriate means to cure the polymeric thermosetting material. Thereafter, the molds are cooled, if required, and opened so that the finished article can be removed therefrom.

BRIEF DESCRIPTION OF THE DRAWINGS

FIG. 1 is a diametral cross sectional view of an exemplary filled article made in accordance with the teachings of the present invention.

FIGS. 2 through 5 are semi-diagrammatic, cross sectional representations of a mold and die set for molding the inner part of the article of FIG. 1 and illustrate the sequence of steps for molding the inner part.

FIGS. 6 through 9 are semi-diagrammatic, cross sectional representations of a mold and die set for the outer part of the article of FIG. 1 and illustrate the sequence of steps for molding the outer part.

FIGS. 10 through 13 are semi-diagrammatic, cross sectional representations of the molds of FIGS. 2–5 and 6–9 and illustrate the steps of filling, joining and curing the inner and outer parts to produce the article of FIG. 1.

FIG. 16 is an enlarged, cross sectional view of the pair of molds illustrated in FIG. 12.

FIGS. 17 through 19 are fragmentary cross sectional views illustrating the sequential formation of the seal between the parts of the structure of FIG. 1 and the removal of flash therefrom.

DETAILED DESCRIPTION OF THE INVENTION

Figure 14:
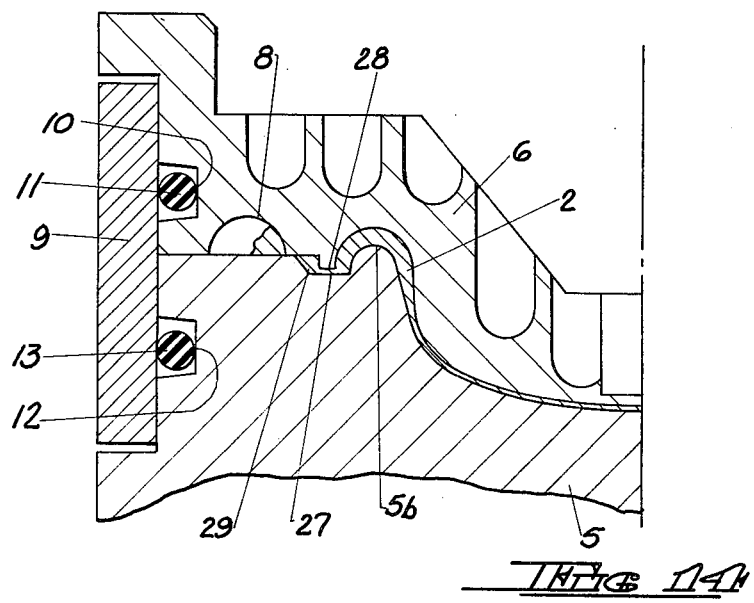
FIG. 14 is a fragmentary, enlarged, cross sectional view of the mold and die set of FIG. 4, illustrating the peripheral edge portion of the molded inner part.

The process of the present invention is applicable to the manufacture of hollow articles which may be filled with liquid, gaseous or solid materials, or combinations thereof. Furthermore, the process is valuable as an approach to the molding of a variety of shapes which are difficult to handle by standard techniques. As indicated above, while not intended to be so limited, the process of the present invention will be described in its application to the molding and filling of vaginal contraceptives of the general type taught in the above mentioned U.S. Pat. Nos. 4,198,976 and 4,200,090. An exemplary contraceptive device of the type contemplated is illustrated in FIG. 1 and is generally indicated at 1. The contraceptive device comprises a container made of a non-porous, resilient elastomer substantially impervious to liquid water. The container is made up of a front or inner half 2 and a rear or outer half 3. The container is substantially filled with an aqueous solution of a spermicidal surfactant 4.

The inner part 2 has a thin membrane portion 2a, having a thickness of from about 0.254 mm to about 0.508 mm (about 0.01 to about 0.02 inches). As indicated above, the membrane portion 2a is such that surfactant micelles cannot diffuse therethrough, while surfactant monomers are free to dissolve in the membrane material and diffuse therethrough. Although the outer part 3 may be made of a different elastomer impervious to diffusion of surfactant monomer molecules, for ease in sealing it is preferred that it be made of the same elastomer having a thickness of from about 1.27 mm to about 2.54 mm (from about 0.05 to about 0.10 inches). The thickness of the outer part 3 serves two purposes. First of all, the thickness of the outer part 3 acts to direct surfactant monomers preferentially through the membrane portion 2a of part 2, the membrane portion 2a being the part of the device placed in proximity to the cervical os. In addition, the thickness of the outer portion 3 tends to provide extra structural support for the device 1, further enhancing retention thereof. Particularly preferred devices have an outer thickness of from about 1.78 mm to about 2.29 mm (about 0.07 to about 0.09 inches) to provide optimum support and retention without adversely increasing awareness of the device. In an exemplary embodiment, the device 1 had an overall height of 19.8 mm (0.779 inches) and an outside diameter of about 50.00 mm (1.968 inches).

While the process of the present invention is generally applicable to any moldable plastic, it is particularly applicable to moldable elastomers, and even more particularly to curable thermosetting elastomers. With respect to the exemplary application of the process of the present invention, illustrated in FIG. 1, the material from which the parts 2 and 3 are molded must have certain parameters including strength, integrity, and the ability to be fashioned into a highly preferred shape. Furthermore, the material should be substantially water-insoluble and both toxicologically and immunologically acceptable. The membrane portion 2a must be capable of the desired metered release of the surfactant monomer molecules. The above mentioned U.S. Pat. Nos. 4,198,976 and 4,200,090 teach numerous silicone polymers, latex rubbers and other types of non-porous polymers which can be used for parts 2 and 3. In a particular embodiment of the device of FIG. 1, produced by the process of the present invention, excellent results were achieved using Dow Corning ®Q7-2245, a high consistency, platinum catalyzed, silicone elastomer available from Dow Corning Corporation. The silicone elastomer was compounded with cross-linker. The curing inhibitor recommended by the Dow Corning Corporation to extend the working time of the compounded silicone elastomer was not used for several reasons. In particular, the exclusion of the curing inhibitor results in faster curing, and a lessened tendency for gas generation during curing.

The silicone elastomer may be compounded with cross linker in a number of ways. For example, compounding may be accomplished with a twin screw compounding extruder, single screw extruder, a ram or standard single screw extruder fitted with a static mixer or a roller mill plus calendering rolls. A preferred method incorporates an extruder and a static mixer with a thin, straight injection tube located in the resin stream between the extruder and the static mixer. The injection tube provides a stream of cross linker and this cross linker stream and the silicone elastomer stream combine in a unidirectional flow before entering the static mixer. This method of compounding is cleaner, faster and safer, and is well adapted to continuous compounding and automation. This method also reduces the number of small air bubbles in the final part which might cause leaks in the membrane part 2a. The extrudate is of cylindrical shape and is sliced into disk-shaped preforms which may be inserted directly into the mold and die sets.

FIGS. 2 through 5 constitute semi-diagrammatic, cross sectional views of a mold and die set for molding the front or inner part 2 of the contraceptive device 1 of FIG. 1. FIGS. 2 through 5 show the sequential steps of the molding procedure and like parts have been given like index numerals.

Turning first to FIG. 2, a lower die member is shown at 5, having a dish or bowl shaped cavity 5a shaped to provide the proper configuration to the inside surface of inner part 2. The die 5 has an annular rounded portion 5b adapted to properly configure the inner surface of the uppermost portion of part 2.

A mold for part 2 is shown at 6 together with a heat transfer medium passage disk 7, the purpose of which will be described hereinafter. The mold 6 is configured to provide the exterior shape of inner part 2. The mold 6 is also provided with an annular overflow notch 8, to accommodate any excess material during the molding of part 2. Finally, an annular vacuum ring 9 is shown mounted on mold 6. To assure a sealing engagement between mold 6 and annular vacuum ring 9, the mold 6 is provided with an annular notch 10 containing an O-ring 11. In similar fashion, the die 5 is provided with an annular notch 12 containing an O-ring 13 so that a sealing engagement can be accomplished between die 5 and vacuum ring 9, as will be described hereinafter. The vacuum ring 9 has a port 14 connected to an appropriate vacuum source (not shown).

The molding of the inner part 2 is preferably accomplished in the following manner. With the die 5 and mold 6 in unheated condition, the molding surfaces of die 5 are preferably coated with a release agent and its cavity 5a is charged with a measured amount of the compounded silicone elastomer which may be in the form of an extruded preform 15. The die 5 and mold 6 are advanced toward each other until both are in sealing engagement with vacuum ring 9. At this point, a vacuum (about 29 inches of mercury) is pulled on the charged cavity between die 5 and mold 6 to minimize the chance of air being entrapped in the silicone during the forming operation. This enhances the appearance of the formed part, minimizing air bubbles and flaws therein. This vacuum step is illustrated in FIG. 3. Following the vaccum step, the die 5 and mold 6 are closed, as shown in FIG. 4, to mold the part 2. Sufficient force must be applied to the opposing mold and die to bring their lands into contact with one another. This molding step can be performed as a single step at about 1500 psi for about 30 to 60 seconds.

Upon completion of the molding of part 2, the mold and die set is opened with the uncured part 2 remaining on mold 6, as shown in FIG. 5.

The molding of outer part 3 is accomplished in substantially the same manner, as shown in FIGS. 6 through 8, wherein like parts have been given like index numerals.

Referring first to FIG. 6, a die 16 is illustrated having a molding surface shaped to provide the desired configuration to the inside surface of outer part 3. A vacuum ring 17, substantially identical to vacuum ring 9 of FIGS. 2 through 5, is provided and has a port 18. A sealing engagement between vacuum ring 17 and die 16 is assured by providing an annular notch 19 in the die, containing an O-ring 20 which cooperates with vacuum ring 17. A mold 21 is shown, having a mold cavity 21a adapted to provide the proper configuration to the exterior surface of outer part 3. The mold 21 is provided with an annular notch 22, similar to annular notch 8 of mold 6 (see FIG. 2). The annular notch 22 will accommodate any excess material during molding of part 3. Annular notches 8 and 22 will cooperate to form an overflow chamber when parts 2 and 3 are sealed together, as will be described hereinafter. Mold 21 has an annular notch 23 formed therein to accommodate O-ring 24 so that a sealing engagement can be achieved between mold 21 and vacuum ring 17. Finally, mold 21 is mounted on a heat transfer medium passage disk 25, the purpose of which will be described hereinafter. The die 16 is preferably coated with a release agent and the cavity 21a of mold 21 is charged with a measured amount of the compounded silicone elastomer. Again, the silicone elastomer may be in the form of an extruded preform 26.

As a first step in the molding procedure, the mold 21 and die 16 are brought together until both elements are in sealing engagement with vacuum ring 17, as shown in FIG. 7. At this point, a vacuum is drawn in the cavity formed between the mold 21 and die 16, in the same manner and for the same purpose described with respect to FIG. 3. Thereafter, the mold and die set is closed while still under vacuum and the molding step is performed (FIG. 7). Again, this step can be performed in a single stage. At the end of the molding procedure, the die 16 and mold 21 are separated with the uncured part 3 remaining in mold 21.

The molds 6 and 21 and dies 5 and 16 may be made from a variety of metals and alloys such as steel, stainless steel, aluminum, beryllium copper, chrome copper, and chrome-plated metals. It is believed that the molds and dies could also be made of appropriate ceramic materials.

The molds 6 and 21 and dies 5 and 16 may be given various types of surfaces. The molds 6 and 21 are preferably treated to improve their ability to retain the molded parts as the dies 5 and 16, respectively, are withdrawn therefrom. Surface treatment of molds 6 and 21 may also be used to impart desired surface characteristics to the molded products. The dies 5 and 16 are preferably treated so that they will more effectively retain a film of mold release agent and thereby aid separation of the dies 5 and 16 from the parts remaining in molds 6 and 21, respectively. It has been found particularly advantageous if the molding surfaces of molds 6 and 21 are microhoned by blasting with a fine abrasive. This treatment imparts to the final product a silky, pleasant-to-touch surface. Furthermore, it helps the escape of small entrapped gas bubbles and, as pointed out earlier herein, assists in retaining the parts 2 and 3 in their respective molds 6 and 21 as the dies 5 and 16 are withdrawn therefrom. The same sort of microhoned surface may be applied to dies 5 and 16. On the other hand, the working surfaces of both the molds 6 and 21 and dies 5 and 16 can be polished or chromed plated. When it is desired to dispense with a release agent, it is preferred to provide the molds 6 and 21 with microhoned surfaces and the dies 5 and 16 with polished (and preferably chromed) working surfaces to facilitate retention of the molded parts by molds as the dies are withdrawn.

It has been found that, in general, release is affected by a number of molding parameters such as compression pressure and time, freshness of the compounded silicone, the material from which the molds and dies are made, the geometry of the molds and dies, the nature of the surfaces of the molds and dies and the mold and die temperature. In addition to this, it has further been found that most conventional mold release agents constitute poor release agents with uncured silicone. It has been determined that release agents containing covalently bonded hydrophilic or polar groups (or hydrophilic atoms) are preferred for good release. Examples of groups found in good release agents are hydroxyl (OH), carboxyl (COOH), ether (COC) and hydroxyl groups combined with carboxyl or ether groups. Furthermore, these groups must be present in sufficient strength or number. Good results have been achieved with the following substances used as release agents: water, gylcerine, glycols, and nonionic surfactants. In some instances solutions of the foregoing materials will also aid release. It has further been determined that it is best that the release agents be in the form of a liquid or soft solid so that they can be readily applied as a thin, uniform film, or near film.

Reference is now made to FIG. 14 which is an enlarged fragmentary view of the die 5 and mold 6 of FIG. 4. It will be noted that die 5 has an annular notch 27 adjacent the portion 5b. The mold 6 has a land 28 partially received within the die notch 27. This results in the formation on molded part 2 of an annular, peripheral, hook-shaped portion 29. The portion 29 is hooked over the outer diameter of land 28. This tends to retain the part 2 on mold 6 when mold 6 and die 5 are separated as in FIG. 5. This hooked engagement further prevents the part 2 from shrinking away from the sides of the mold, uncured silicone having a tendency to return to its shape prior to molding.

Figure 15:
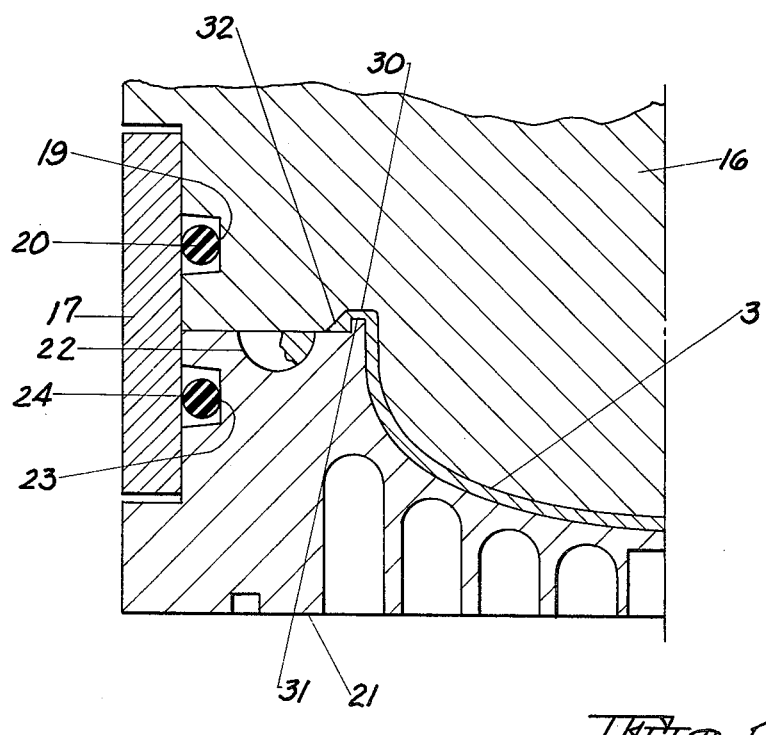
FIG. 15 is a fragmentary, enlarged, cross sectional view of the mold and die set of FIG. 8, illustrating the peripheral edge portion of the molded outer part.

A similar situation obtains with respect to mold 21 and die 16. FIG. 15 is a fragmentary, enlarged, cross-sectional view of die 16 and mold 21 as shown in FIG. 8. In this instance, die 16 is provided with an annular notch 30, while mold 21 is provided with a land 31 partially received within notch 30, when the die 16 and mold 21 are in their closed positions. As a result, the part 3 has a peripheral hook shaped annular portion 32, engaging the outer diameter of land 31 to maintain the part 3 properly positioned within mold 21 when the mold is separated from die 16, as in FIG. 9.

With the forming portion of the process of the present invention completed and with the parts 2 and 3 remaining in their original molds 6 and 21, the filling, sealing and curing portions of the process are next performed. Reference is now made to FIGS. 10 through 13, wherein like parts have been given like index numerals. Reference is first made to FIG. 10. The molds 6 and 21 are located in cooperating, aligned relationship. Thereafter, the part 3 in mold 21 is provided with a metered amount of the aqueous solution of spermicidal surfactant 4.

The above mentioned U.S. Pat. No. 4,198,976 and U.S. Pat. No. 4,200,090 teach a number of surfactants for this purpose, among which $C_{10}EO_5$ and $C_{10}EO_6$ are preferred. The surfactants are, of course, compatible with the material from which parts 2 and 3 are made.

It will be noted that vacuum ring 9 has been retained on mold 6. Once part 3 has been filled with surfactant solution 4, the molds 6 and 21 are brought together to the extent that they are both in sealing relationship with vacuum ring 9. At this point, the chamber formed between molds 6 and 21 is flushed with a partial vacuum, followed by purging with carbon dioxide, followed by a final flush with the partial vacuum. This system of flushing with a partial vacuum, purging with carbon dioxide, followed by a final flush with the partial vacuum, removes air, which could initiate oxidation of the spermicidal surfactant 4, from between parts 2 and 3. A partial vacuum of from about 24 to about 27 inches of mercury is used. Without cooling, a full vacuum could cause the surfactant solution to boil or froth and could also result in flaws, bubbles, pocks and leaks in the silicone parts 2 and 3. Thus, this vacuum level is a compromise between silicone wall quality, frothing and the amount of gas remaining in the sealed product. Furthermore, should the surfactant solution froth, this can result in product loss, and in some instances weakening of the seal. After the partial vacuum-carbon dioxide purge step of FIG. 11, the mold is fully closed to seal parts 2 and 3 and trim off scrap. This is shown in FIG. 12.

It has been found that if the part 3 is filled too full of surfactant 4, or if the vacuum level is too low, as the mold closes excessive internal pressure will prevent a complete seal from forming. At a slightly lower fill level or higher vacuum, a good product will be formed, but the completed product will have flash which must be removed in a subsequent operation. However, if the fill level, vacuum level and curing temperature are properly balanced, a sound, filled product can be formed without flash. The ideal gas-liquid balance and level will vary with curing temperature and possibly curing time since these factors, also, influence the internal pressure. It has been found advantageous to have a small amount of carbon dioxide in the product cavity, since the gas and liquid aid in the final product formation by serving as a strong, resilient, molding core. Without some gas within the product, seal leaks may occur because of attempting to close the molds 6 and 21 against an incompressible liquid core. Carbon dioxide is preferred because it is inert with respect to the surfactant and it diffuses out of the finished product more rapidly than would air or most other gases.

Reference is now made to FIG. 16 which constitutes an enlarged and more detailed view similar to FIG. 12. In FIG. 16, like parts have again been given like index numerals. The molds 6 and 21 are illustrated in their closed and clamped position wherein the parts 2 and 3 are brought together and permanently sealed. It will be noted from this Figure that seal lands 28 of mold 6 and 31 of mold 21 have zero clearance therebetween. Exteriorly of the lands 28 and 31 there is clearance between the molds, as at 33. This clearance extends all the way to the outermost edges of molds 6 and 21. It will further be noticed in FIG. 16 that the annular notches 8 in mold 6 and 22 in mold 21 form an overflow chamber extending about the joined and sealed product. The overflow chamber 8-22 is adapted to receive any excess silicone during the sealing step.

In addition to FIG. 16, reference is now made to FIGS. 17 through 19 which are fragmentary, enlarged, cross sectional views of the molds 6 and 21, and which illustrate the sealing sequence of parts 2 and 3.

FIG. 17 depicts the molds 6 and 21 in their positions shown in FIG. 11 during the vacuum-carbon dioxide purge operation. The hook shaped portion 29 of part 2 engages the outer diameter of land 28 while the hook shaped portion 32 of part 3 engages the outer diameter of land 31, maintaining the parts 2 and 3 in their proper position in their respective molds.

As the molds 6 and 21 are moved toward their clamped and sealing positions (as shown in FIG. 12) the parts 2 and 3 begin to be pressed together, as shown in FIG. 18. It will also be noted from FIG. 18 that the level of surfactant 4 within the parts 2 and 3 is rising.

When the dies 6 and 21 are brought together to their final closed and clamped position (as shown in FIG. 12) there is zero clearance between lands 28 and 31. As a result of this, the silicone material is squeezed both inwardly and outwardly with respect to the lands (both to the left and right of the lands as viewed in FIG. 19) and the lands pinch-off and trim the excess silicone from the product 1, defining the outer surface condition of the sealed area. The inward squeezing of the silicone material (i.e. to the left in FIG. 19) contributes to the integrity of the sealed area, as shown at 34. The excess silicone trimmed by lands 28 and 31 will go into the clearance area 34 between dies 6 and 21, and if sufficient excess material is present, will be accommodated by the overflow chamber 8-22.

FIG. 19 shows the ideal seal formed between parts 2 and 3. This ideal seal (both substantially rimless and flashless) is readily achievable upon proper determination of the above discussed parameters including the nature of the silicone material, partial vacuum level, gas-liquid balance and level, curing temperature and curing time. Armed with the teachings of the present invention, these parameters can readily be determined by one skilled in the art (for the part being made) through routine experimentation. While it is clearly preferable to avoid the presence of extraneous materials in the seal area, it has nonetheless been found that the excellent silicone-to-silicone seals of the type generally shown in FIG. 19 can in some instances be achieved even though excess surfactant solution or release agent may be present as the molds are being closed. While not wishing to be bound by any particular theory of operation, it is believed that these materials are displaced from the seal area as the molds are fully closed.

Once the dies 6 and 21 have achieved the positions shown in FIGS. 12, 16 and 19, and the parts 2 and 3 have been sealed together, it is necessary to cure the uncured silicone parts 2 and 3. This is accomplished by heating the dies 6 and 21. Any appropriate heating system can be practiced, including the use of steam or the transfer of heat by contact of the molds with hot platens.

A preferred heating method entails the use of a hot liquid such as heated water, heated oil or the like. Excellent results have been achieved, for example, using silicone oil which is both medically safe and harmless to the dies. To this end, the back side of mold 6 and the backside of mold 21 are provided with spiral grooves 35 and 36, respectively.

Spiral groove 35 begins near the periphery of mold 6 and terminates at its center. The same is true of spiral groove 36 in mold 21. The portions 35a of mold 6 between the convolutions of groove 35 are such that adequate support is provided for the mold surface of mold 6 and the distance between the groove 35 and the mold surface can be relatively thin for good heat transfer. Furthermore, the mold portions 35a are backed and additionally supported by the heat transfer medium passage disk 7. The same is true of mold portions 36a of mold 21 which are additionally backed by the heat transfer medium passage disk 25. This allows the convolutions of groove 36 to closely approach the mold surface of mold 21 for good heat transfer.

The heat transfer medium passage disk 7 is affixed to mold 6 by any suitable means such as machine screws, one of which is shown at 37. The disk 7 is provided with an annular notch 38 to accommodate an O-ring 39 so that the disk 7 has a sealing engagement with mold 6.

In addition to the support provided by disk 7 to mold portions 35a of mold 6, the disk 7 also provides inlet and outlet passages for the hot oil or other heating fluid to and from spiral passage 35. To this end, disk 7 has a horizontal inlet bore 40 communicating with a vertical inlet bore 41. The bores 40 and 41 serve as an inlet passage for the heated oil to the outermost convolution of spiral groove 35. In similar fashion, disk 7 is provided with a second horizontal bore 42 and a second vertical bore 43. The bores 42 and 43 serve as an outlet passage for the heating fluid from the innermost end of spiral groove 35. It will be understood that the bores 40 and 42 are connected to a source of the circulating heating fluid (not shown).

The heat transfer medium passage disk 25 is affixed to mold 21 by machine screws or the like, one of which is shown at 44. The disk 25 has a first horizontal bore 45 and a connecting vertical bore 46, both serving as an inlet passage for heating fluid to the outermost convolution of spiral groove 26. The disk 25 has a second horizontal bore 47 and a connected second vertical bore 48. These bores constitute an outlet passage communicating with the innermost end of spiral passage 36. Again, bores 45 and 47 will be connected to the source of circulating heating fluid.

Typical cure times are from about 2 to about 10 minutes with fluid temperatures from about 200° F. to about 370° F. For example, with the particular silicone used, excellent results were achieved utilizing a hot oil heating fluid at a temperature of 370° F. for about 2.5 minutes. Similar results, on the other hand, were achieved at a temperature of about 200° F. for about 8 minutes. It will be noted that the curing time and temperature bear an inverse relationship. During the sealing and curing steps, the molds 6 and 21 are clamped at a pressure sufficient to pinch off excess silicone and to keep the mold lands together during curing (to prevent leaks and flash).

After the curing step, it is generally desirable to cool the molds 6 and 21 so that they are not opened at a temperature at or above the boiling point of the surfactant solution. Cooling of the molds can be accomplished in any appropriate manner. For example, the molds could simply be allowed to stand and cool to room temperature. Alternatively, cold water could be run through the spiral grooves 35 and 36, followed by air to remove the water therefrom. Preferably, cooled silicone oil or the like is used.

Once the molds 6 and 21 have appropriately cooled, they can be opened as shown in FIG. 13 and the completed device 1 can be removed from mold 21. Removal of the device 1 from mold 21 can be accomplished in a number of ways including: by hand, by friction, by gripper means, and by a blast of air.

Upon removal of the completed device 1 from the molds 26 and 21, the molds are cleaned of flash and excess silicone material and the process can be then repeated. A typical cycle time for the practice of the process of the present invention is about 5 minutes.

Forming-sealing pressure, curing time and curing temperature will depend upon the curing or molding requirements of the polymer used, the shape of the article formed, and the amount of material used for the process. In an exemplary run making contraceptive devices of the type described above, filled with a spermicide solution and utilizing Dow Corning ®Q7-2245 silicone elastomer, excellent results were achieved using stainless steel molds. A forming and sealing force of approximately 3500 pounds was applied in the exemplary embodiment to the lands of the opposing molds. This was achieved by applying approximately 1600 lb/in$^2$ hydraulic pressure to a 1.68" diameter piston attached via a rod to one of the molds. A heat cycle of approximately 2.5 minutes was used for curing. Silicone oil at approximately 350° F. was circulated through the molds resulting in a mold temperature of approximately 250° F. After the heat cycle, the molds were cooled to from about 115° F. to about 120° F. by circulating 80° F. silicone oil through the molds. After the cooling cycle, lasting about 1 minute, the filled and sealed article was removed from the molds.

When parts 2 and 3 are comprised of thermosetting polymers which are curable at a temperature below the boiling point of the material 4 to be encapsulated, cooling of the dies may not be necessary. Furthermore, if the form, fill and seal steps can be accomplished fast enough (i.e., before the silicone is cured), and if the silicone can be cured and removed from the molds before the filler material 4 boils, the molds 6 and 21 could be constantly maintained at the curing temperature. It is also within the scope of the present invention to partially cure the silicone during the curing step and then to heat sterilize the completed unit 1, depending upon the heat sterilizing step to complete the cure.

Modifications may be made in the invention without departing from the spirit of it. For example, the process can be adapted to the molding of parts 1 and 2 by vacuum forming, rather than compression molding. In general, however, compression molding is preferred since vacuum forming of uncured silicone is more difficult, generates more scrap, may require the use of a curing inhibitor, and places greater restriction on the design of the unit. If vacuum forming were used, the process would be unchanged from the filling step on. The process steps ahead of filling would differ. The silicone would be extruded as sheets which would be draped over a mold for each part half and then would be subsequently drawn into the molds by vacuum. The mold for each part half would consist of just one part (i.e. an exterior mold), no die part being required. Since a one-part mold would be used, there would be no need for mold release of the uncured silicone.

Injection molding to make the individual part halves may also be used. Injection molding would not greatly alter the process from the point where the two uncured halves have been generated. However, it would require somewhat different molding equipment and techniques in order to form the uncured part halves.

In some applications, thermoplastic material, rather than thermosetting material, could be used for the individual parts. In many instances, thermosetting material is preferred over thermoplastic material, however since thermoplastic material has no cross linking and therefore has a greater tendency to creep under stress.

An exemplary form-fill-seal process for making the part halves using thermoplastic polymers may be outlined as follows: a hot extrusion and injection molding system is used to melt the thermoplastic and to inject it into two sets of cold, closed molds, thereby forming the completed (solidified) halves to be used in forming the final product. The two sets of molds for making the two halves are opened with the cooled and solidified part halves maintained within the specific exterior mold halves that will be used to form and seal the final unit. This might involve the use of release agents selected for effectiveness with the thermoplastic material in question, texturized molds, knock-out rings, air blow-off jets, or the like.

The exterior mold halves, still holding the part halves, are brought into opposition. From this point on, the filling, evacuation, purging and sealing procedures can be the same as those described above.

The chamber for the heat transfer fluid in molds utilizing thermoplastic material will differ from molds utilizing thermosetting material in one important respect. The chamber of each mold half should have two compartments. One compartment is a channel that lies only above the seal land, and either heating or cooling fluid can be circulated through this compartment as needed. The other chamber covers the bulk of the mold half and is used primarily to cool the part. As the molds are finally brought together, hot fluid is run through the chambers located behind the seal lands to melt the thermoplastic polymers over the seal lands. Once the melted polymer over the two lands has been pressed together, the hot, heat transfer fluid is replaced by cold fluid (below the melt temperature of the polymer), thereby completing the seal by causing the polymer to solidify. Thereafter, the molds are opened and the final part is removed. As indicated above, the molding of the individual parts 2 and 3 can be accomplished in a single-stage operation, rather than in a two-stage operation. Furthermore, depending upon the materials used for the individual parts and depending upon the materials from which the molds 6 and 21 and the dies 5 and 16 are made (and the nature of their surfaces), the use of a release agent may not be necessary.

It will be understood by one skilled in the art that the process of the present invention could be practiced by a unit comprising a form-fill-seal-cure press together with supporting systems including a hot heat transfer fluid unit, a cold transfer fluid unit, a high vacuum pump, a low vacuum pump, a hydraulic pump, a power system including circuitry for measuring, timing and controlling the subsystem interactions, and various safety interlocks controlled by heating and cooling fluid temperatures.

While the process is well suited for the making of a contraceptive device of the type described above, as an exemplary embodiment, the process is not limited, in making contraceptive devices, to the particular contraceptive device configuration illustrated. For example, the process of the present invention is well suited for making contraceptive devices of the general class described above, but which are lobed, which may have reinforced areas, or which may be partitioned by reinforced areas into a plurality of closed compartments.

As indicated above, the process of the present invention is particularly suited for making hollow articles. The articles may be filled, or not, as desired. The precise nature of the articles made by the present process does not constitute a limitation.

What is claimed is:

1. A process of making a hollow article from moldable plastic material and filled with a filler substance comprising the steps of molding two parts using at least an exterior mold for each part, which parts, when joined at their peripheries, will constitute said article, causing said parts to remain in their respective exterior molds, bringing said exterior molds into opposed position, locating said filler substance in one of said parts, sealing said exterior molds together when in opposed position and prior to complete closure thereof, subjecting the space between the exterior molds with the parts therein to a partial vacuum, thereafter purging said space with a gas non-reactive to said filler material and said parts, and again subjecting said space to a partial vacuum prior to closing said exterior molds, closing said exterior molds and subjecting them to a clamping pressure to join said parts about their peripheries and to remove flash therefrom, heating parts at least of said exterior molds, cooling said exterior molds, opening said exterior molds and removing therefrom said article.

2. The process claimed in claim 1 wherein said parts are injection molded.

3. The process claimed in claim 1 wherein said parts are vacuum molded.

4. The process claim in claim 1 wherein said parts are compression molded.

5. The process claimed in claim 1 wherein said moldable plastic material is a thermoplastic elastomer.

6. The process claimed in claim 1 wherein said moldable plastic material is a thermosetting elastomer.

7. The process claimed in claim 1 wherein said moldable plastic material is silicone.

8. The process claimed in claim 1 wherein said moldable plastic material is a thermosetting elastomer and wherein said step of molding two parts comprises providing said exterior mold and a forming die for each part, bringing said mold and die for each part into opposed and sealing relationship with a measured amount of said thermosetting elastomer therebetween, pulling a vacuum in said sealed mold and die for each part, closing said mold and die for each part and forming said part therein, removing said die from each part, and including the steps of heating said closed and clamped exterior molds to cure said thermosetting elastomer prior to cooling said exterior molds and removing said article therefrom.

9. The process claimed in claim 1 wherein said filler material is chosen from the class consisting of a liquid material, a solid material and combinations thereof.

10. The process claimed in claim 8 wherein said molds are microhoned by blasting with a fine abrasive.

11. The process claimed in claim 8 wherein said dies are coated with a thin film of release agent chosen from the class consisting of glycerine, glycols, nonionic surfactants, solutions thereof and water.

12. The process claimed in claim 10 wherein said dies are chrome plated.

13. The process claimed in claim 10 wherein said dies are polished.

14. A process of making a vaginal contraceptive of the type comprising a container made up of a front half and a rear half and being substantially filled with an aqueous solution of a spermicidal surfactant, comprising the steps of molding said front and rear halves of a thermosetting elastomer using at least an exterior mold for each half, causing said front and rear halves to remain in their respective exterior molds, bringing said exterior molds with their respective halves therein into opposed and spaced position, locating said aqueous solution of spermicidal surfactant in one of said halves, sealing said exterior molds while in said opposed and spaced position, subjecting the space between said exterior molds to a partial vacuum, thereafter purging said space with a gas non-reactive to said solution and said halves, again subjecting said space to a partial vacuum, closing said exterior molds and subjecting them to a clamping pressure sufficient to join said halves together and to remove flash therefrom, heating said exterior molds to cure said halves, cooling said exterior molds to a temperature at least below the boiling point of said solution, opening said exterior molds and removing said vaginal contraceptive therefrom.

15. The process claimed in claim 14 including the steps of providing an exterior mold and a forming die for each of said front and rear halves, bringing said mold and die for each half into opposed and sealing relationship with a measured amount of said thermosetting elastomer therebetween, pulling a vacuum in each sealed mold and die and forming said halves therein and removing said die from each of said halves.

16. The process claimed in claim 14 wherein said thermosetting elastomer is a silicone elastomer.

17. The process claimed in claim 14 wherein said purge gas is carbon dioxide.

* * * * *

UNITED STATES PATENT AND TRADEMARK OFFICE
CERTIFICATE OF CORRECTION

PATENT NO. : 4,447,373
DATED : May 8, 1984
INVENTOR(S) : CHARLES W. CHAPPELL and ELDON G. SPLETZER It is certified that error appears in the above-identified patent and that said Letters Patent are hereby corrected as shown below:

Column 11, line 20, "26" should read -- 36 --.

Column 14, line 14, "claim", first occurrence, should read -- claimed --.

Signed and Sealed this

Twenty-first Day of August 1984

[SEAL]

Attest:

GERALD J. MOSSINGHOFF

Attesting Officer

Commissioner of Patents and Trademarks